(12) United States Patent
Bitto et al.

(10) Patent No.: US 7,360,451 B2
(45) Date of Patent: Apr. 22, 2008

(54) MEASURING TRANSDUCER OF VIBRATION-TYPE

(75) Inventors: Ennio Bitto, Aesch (CH); Christian Schütze, Basel (CH); Martin Anklin-Imhof, Dornach (CH); Christof Huber, Bern (CH); Dieter Mundschin, Liestal (CH); Michael Lambrigger, Basel (CH)

(73) Assignee: Endress + Hauser Flowtec AG, Reinach (CH)

( * ) Notice: Subject to any disclaimer, the term of this patent is extended or adjusted under 35 U.S.C. 154(b) by 0 days.

(21) Appl. No.: 11/636,555

(22) Filed: Dec. 11, 2006

(65) Prior Publication Data

US 2007/0151371 A1 Jul. 5, 2007

Related U.S. Application Data

(60) Provisional application No. 60/752,372, filed on Dec. 22, 2005, provisional application No. 60/752,374, filed on Dec. 22, 2005.

(51) Int. Cl.
*G01F 1/84* (2006.01)
(52) U.S. Cl. .................................. 73/861.355
(58) Field of Classification Search ........... 73/861.357, 73/861.355, 861.356
See application file for complete search history.

(56) References Cited

U.S. PATENT DOCUMENTS

| | | | |
|---|---|---|---|
| 4,768,384 A | 9/1988 | Flecken |
| 4,777,833 A | 10/1988 | Carpenter |
| 4,801,897 A | 1/1989 | Flecken |
| 4,879,911 A | 11/1989 | Zolock |
| 5,009,109 A | 4/1991 | Kalotay |
| 5,287,754 A | 2/1994 | Kazakis |

(Continued)

FOREIGN PATENT DOCUMENTS

DE 196 04 529 C2 8/1997

(Continued)

*Primary Examiner*—Jewel Thompson
(74) *Attorney, Agent, or Firm*—Bacon & Thomas, PLLC (57) ABSTRACT

A measuring transducer includes a transducer housing, as well as an internal part arranged in the transducer housing. The internal part includes at least one curved measuring tube vibrating, at least at times, during operation and serving for conveying the medium, as well as a counteroscillator affixed to the measuring tube on the inlet-side, accompanied by formation of a coupling zone, and to the measuring tube on the outlet-side, accompanied by the formation of a coupling zone. The internal part is held oscillatably in the transducer housing, at least by means of two connecting tube pieces, via which the measuring tube communicates during operation with the pipeline and which are so oriented with respect to one another, as well as with respect to an imaginary longitudinal axis of the measuring transducer, that the internal part can move during operation in the manner of a pendulum about the longitudinal axis. The measuring tube and the counteroscillator are additionally so embodied and so oriented with respect to one another that both a center of mass spaced from the imaginary longitudinal axis of the measuring tube, as well as also a center of mass of the counteroscillator spaced from the imaginary longitudinal axis, lie in a common region of the measuring transducer spanned by the imaginary longitudinal axis and the measuring tube, and that the center of mass of the measuring tube is spaced farther from the longitudinal axis than the center of mass of the counteroscillator.

23 Claims, 4 Drawing Sheets

U.S. PATENT DOCUMENTS

| | | |
|---|---|---|
| 5,357,811 A | 10/1994 | Hoang |
| 5,549,009 A | 8/1996 | Zaschel |
| 5,687,100 A | 11/1997 | Buttler |
| 5,705,754 A | 1/1998 | Keita |
| 5,734,112 A | 3/1998 | Bose |
| 5,736,653 A | 4/1998 | Drahm |
| 5,892,159 A | 4/1999 | Smith |
| 5,987,998 A | 11/1999 | Campbell |
| 6,092,429 A | 7/2000 | Cunningham |
| 6,308,580 B1 | 10/2001 | Crisfield |
| 6,327,915 B1 | 12/2001 | Van Cleve |
| 6,415,668 B1 | 7/2002 | Cage |
| 6,477,902 B1 | 11/2002 | Oosawa |
| 6,666,098 B2 | 12/2003 | Drahm |
| 7,127,952 B2 | 10/2006 | Bitto |
| 2007/0151370 A1* | 7/2007 | Bitto et al. ............ 73/861.357 |

FOREIGN PATENT DOCUMENTS

| | | |
|---|---|---|
| DE | 697 03 981 T2 | 1/2001 |
| DE | 698 14 149 T2 | 11/2003 |
| DE | 699 11 981 T2 | 5/2004 |
| DE | 697 23 706 T2 | 6/2004 |
| DE | 600 12 161 T2 | 8/2005 |
| DE | 10 2004 023 600 A1 | 12/2005 |
| DE | 10 2004 035 971 A1 | 2/2006 |
| EP | 0 905 488 A2 | 3/1999 |
| EP | 1 130 367 A1 | 9/2001 |
| EP | 1 260 798 A1 | 11/2002 |
| EP | 1 279 935 A2 | 1/2003 |
| EP | 1 130 367 B1 | 10/2003 |
| EP | 1 431 719 A1 | 6/2004 |
| WO | WO 01/02816 A2 | 1/2001 |

* cited by examiner

MEASURING TRANSDUCER OF VIBRATION-TYPE

This application is a nonprovisional of U.S. Provisional Application 60/752,372 filed on Dec. 22, 2005 and U.S. Provisional Application 60/752,374 filed on Dec. 22, 2005 and which claims the benefit of German application numbers 102005062007.8 filed on Dec. 22, 2005 and 102005062004.3 filed on Dec. 22, 2005.

FIELD OF THE INVENTION

The invention relates to a measuring transducer of vibration-type, especially one for use in a Coriolis mass flow meter.

BACKGROUND OF THE INVENTION

For determining a mass flow of a medium flowing in a pipeline, especially a liquid or other fluid, often such measuring devices are used which, by means of a measuring transducer of vibration-type and a control and evaluation electronics connected thereto, effect in the fluid Coriolis forces and, derived from these forces, produce a measurement signal representing mass flow. Such measuring transducers, especially also their use in Coriolis mass flow meters, have been known already for a long time and are in industrial use. Thus e.g. EP-A 11 30 367, US-A 2005/0139015, U.S. Pat. Nos. 6,666,098, 6,477,902, 6,415,668, 5,549,009 or 5,287,754 describe Coriolis mass flow meters having, in each case, a measuring transducer of vibration-type, which measuring transducer reacts to a mass flow of a medium flowing in a pipeline and includes a transducer housing as well as an internal part arranged in the transducer housing. The internal part includes: At least one curved measuring tube vibrating during operation, at least at times, and serving for conveying the medium; as well as a counteroscillator affixed on the inlet end to the measuring tube for forming a first coupling zone and at the outlet end to the measuring tube for forming a second coupling zone. The counteroscillator essentially rests during operation, or it oscillates essentially equally-oppositely to the measuring tube, thus with equal frequency and opposite phase. The internal part is additionally held oscillatably in the transducer housing, at least by means of two connecting tube pieces, via which the measuring tube communicates with the pipeline during operation.

Curved, e.g. U, V or Ω shaped, vibrating measuring tubes can, as is known, when excited to bending oscillations according to a first eigenoscillation form, effect Coriolis forces in the medium flowing therethrough. Selected as a first eigenoscillation form of the measuring tube in the case of such measuring transducers is usually that eigenoscillation form wherein the measuring tube moves in the manner of a pendulum at a lowest natural resonance frequency about an imaginary longitudinal axis of the measuring transducer in the manner of a cantilever clamped at one end. The Coriolis forces produced in this way in the medium flowing therethrough lead, in turn, thereto, that the excited pendulum-like, cantilever oscillations of the so-called wanted mode are superimposed with bending oscillations according to at least one second eigenoscillation form of equal frequency. In the case of measuring transducers of the described kind, these cantilever oscillations compelled by Coriolis forces correspond to the so-called Coriolis mode, usually that eigenoscillation form at which the measuring tube also executes rotary oscillations about an imaginary vertical axis perpendicular to the longitudinal axis. Due to the superimposing of wanted and Coriolis modes, the oscillations of the measuring tube registered by means of the sensor arrangement at the inlet and outlet ends exhibit a measurable phase difference as a function also of the mass flow.

Frequently, the measuring tubes of such measuring transducers, e.g. installed in Coriolis mass flow meters, are excited during operation to an instantaneous resonance frequency of the first eigenoscillation form, especially at an oscillation amplitude regulated, or controlled, to a constant level. Since this resonance frequency, especially also, depends on the instantaneous density of the fluid, it is possible, e.g. in the case of usual commercially available Coriolis mass flow meters, also to measure, besides the mass flow, also the density of flowing fluids.

An advantage of a curved tube shape is that e.g. thermally related changes in length, especially also in the case of the use of measuring tubes having a high coefficient of thermal expansion, cause practically no, or only very small, mechanical stresses in the measuring tube itself and/or in the connected pipeline. A further advantage of curved measuring tubes is, however, to be seen in the fact that the measuring tube can be made relatively long and consequently a high sensitivity of the measuring tube can be achieved for the mass flow to be measured at a relatively short installed length and at relatively low exciter energy. These circumstances make it possible also to manufacture the measuring tube of materials of high coefficient of thermal expansion and/or high modulus of elasticity, i.e. materials such as e.g. stainless steel. In comparison thereto, in the case of measuring transducers of vibration-type having straight measuring tubes, the measuring tube is usually made of a material having at least a lower coefficient of thermal expansion and, as required, also a lower modulus of elasticity than stainless steel, in order to prevent axial stresses and achieve a sufficient sensitivity of measurement. Consequently, for this case, measuring tubes are preferably of titanium or zirconium, which are, however, on the basis of the higher cost of material and the usually also higher processing expense, much more expensive than those of stainless steel. Additionally, a measuring transducer with a single measuring tube has, as is known, compared to one with two measuring tubes flowed through in parallel, the additional great advantage that distributor pieces serving for the connecting of the measuring tubes with the pipeline are not necessary. Such distributor pieces are on the one hand complicated to manufacture and on the other hand also represent flow bodies having a marked inclination for the formation of accretions or for plugging.

Due to the mostly rather narrow band width of counteroscillators in the wanted mode, measuring transducers with a single curved measuring tube have, however, often for applications where density of the medium fluctuates over a wide range, especially also in comparison to such measuring transducers with two parallel measuring tubes, the disadvantage that, as a result of the imbalance of the internal part fluctuating with the density, the zero point of the measuring transducer and consequently also the measuring accuracy of the respective inline measuring device can equally fluctuate significantly and as, a result, can be correspondingly decreased. This is a result of, among other things, that also by means of the usually single counteroscillator, transverse forces can only be incompletely neutralized and, therefore, only incompletely kept away from the connected pipeline. Such transverse forces are induced in the measuring transducer due to alternating ended, lateral movements of the single measuring tube conveying the medium and are rather broadbanded as a result of strongly fluctuating medium densities, in comparison to the counterforces arising on the basis of the counteroscillator. The residual transverse forces can, in turn, lead to the fact that the above mentioned, internal part, moving, as a whole, in the manner of a pendulum about the longitudinal axis of the measuring transducer, begins also to oscillate laterally. These lateral oscillations of the internal part produce, correspondingly, also an additional elastic deformation of the connecting tube piece and can in this way effect also undesirable vibrations in the connected pipeline. Moreover, on the basis of such lateral oscillations of the internal part, it is also possible to provoke also cantilever oscillations in the measuring tube through which the fluid is not flowing. These are very similar to the Coriolis mode and, in any event, however, of equal frequency and consequently practically indistinguishable from the Coriolis mode, which, in turn, would make the measuring signal representing the actual mass flow unusable.

This arises also in the case of measuring transducers which are implemented according, for example, to the principle proposed in U.S. Pat. Nos. 5,705,754 or 5,287,754. In the case of measuring transducers described there, the transverse forces produced by, or on the part of, the vibrating, single measuring tube and which are rather mid or high frequency oscillatory forces, are attempted to be kept away from the pipeline by means of a single counteroscillator, which is rather heavy in comparison to the measuring tube and in any event is tuned to a higher frequency in comparison to the measuring tube, and, as required, by means of a relatively soft coupling of the measuring tube to the pipeline, thus, essentially by means of a mechanical low pass. Unfortunately, in this case, however, the mass of the counteroscillator required for achieving a sufficiently robust damping of the transverse forces rises more than proportionately with the nominal diameter of the measuring tube. This represents a great disadvantage for such measuring tubes of high nominal diameter, since a use of such components of high mass means, namely, always an increased cost of assembly, both in the manufacture, as well as also in the case of the installing of the measuring device into the pipeline. Moreover, in this case, it is only possible to assure, at great complexity, that the smallest eigenfrequency of the measuring transducer which, yes, also does become always lower with increasing mass, lies, after as before, very far from the likewise low eigenfrequencies of the connected pipeline. Consequently, a use of such a measuring transducer in industrially usable, inline measuring devices of the described kind, for example, Coriolis mass flow measuring devices, has long been rather limited to relatively low measuring-tube nominal diameters up to about 10 mm. Measuring transducers of the above described kind are moreover also sold on the part of the assignee itself under the mark "PROMASS", series designation "A", for a nominal diameter range of 1-4 mm and have proven themselves there, especially also in the case of applications with very low flow rates and/or high pressure.

In contrast, in the case of measuring transducers shown in U.S. Pat. Nos. 6,666,098, 6,477,902, or 5,549,009, the two, here essentially straight, connecting tube pieces are so oriented with respect to one another, as well as with respect to an imaginary longitudinal axis of the measuring tube, that the internal part, formed by means of the measuring tube and counteroscillator, as well as the oscillation exciters and oscillation sensors correspondingly applied thereto, can move, during operation, in a pendulum-like manner about the longitudinal axis. In other words, the entire internal part can execute pendulum oscillations during operation about the longitudinal axis L, conditioned on the, especially, density-dependent imbalances between measuring tube 10 and counteroscillator 20, which, depending on the way in which the imbalance shows itself, are of equal phase with the cantilever oscillations of the measuring tube 10 or of the counteroscillator 20. In such case, the torsional stiffnesses of the connecting tube pieces are preferably so tuned to one another and to the internal part carried by the two, that the internal part is suspended essentially rotationally softly about the longitudinal axis.

This is achieved, for example, in the case of U.S. Pat. No. 6,666,098, in such a manner that the torsional stiffness of the connecting tube pieces is so dimensioned that a respective eigenfrequency of a torsional oscillator inherently formed on the inlet end and on the outlet end by means of the respective connecting tube pieces and associated terminal mass fractions of the internal part which can be considered as essentially rigid and stable in form and oscillating about the longitudinal axis rotationally, lies in each case in the region of the oscillation frequency of the measuring tube oscillating in the wanted mode. Additionally, at least in the case of the measuring transducer proposed in the case of U.S. Pat. No. 6,666,098, measuring tube and counteroscillator are so tuned to one another that they oscillate at least in the wanted mode with approximately equal resonance frequency. Measuring transducers of the described kind are, furthermore, also sold by the assignee itself under the mark "PROMASS", series designation "H", for a nominal diameter range of 8-50 mm and have proven themselves there, especially also in the case of applications exhibiting a variable density of the medium to a considerable degree during operation. The pendulum-like movement of the internal part is, in this way, especially developed, or at least favored, such that both a measuring-tube center of mass spaced from the imaginary longitudinal axis, as well as also a center of mass of the counteroscillator spaced from the imaginary longitudinal axis, lie in a common region of the measuring transducer spanned by the imaginary longitudinal axis and the measuring tube.

However, investigations have in the meantime shown that the zero point of measuring transducers of the named kind can be subject, at very low mass flow rates and media deviating as to density considerably from the calibrated reference density, after, as before, to considerable fluctuations. Experimental investigations on measuring transducers configured according to U.S. Pat. No. 6,666,098, for which, as proposed, a relatively heavy counteroscillator has been used, have, it is true, led to the recognition that, in this way, there is quite a certain improvement of the null point stability and, as a result, an improvement of the measuring accuracy of inline measuring devices of the described kind, but, however, this has been achieved only to an unsatisfactory degree. In any case, in the configurations proposed in U.S. Pat. No. 6,666,098, a significant improvement of the measuring accuracy is essentially achievable only in the face of having to accept the already discussed disadvantages as discussed with reference to U.S. Pat. Nos. 5,705,754 or 5,287,754.

SUMMARY OF THE INVENTION

An object of the invention, therefore, is to improve the density dependence of the zero point and, as a result, the zero point stability of measuring transducers of the described kind and, indeed, in such a manner that the measurement pickup is, on the one hand, dynamically well balanced over a wide range of densities of the medium and, on the other hand, is, in spite of this, as in comparison to the measuring transducers proposed in U.S. Pat. Nos. 5,705,754 or 5,287,754, of lower mass. Especially in such case, the compensating principle proposed in U.S. Pat. No. 6,666,098, with the terminal, inherent torsional oscillators tuned essentially to the wanted frequency of the measuring tube and counteroscillator tuned to the wanted frequency, can be effectively applied after as before.

For achieving the object, the invention resides in a measuring transducer of vibration-type for a medium flowing in a pipeline. The measuring transducer includes a transducer housing, as well as an internal part arranged in the transducer housing. The internal part includes at least one curved measuring tube for conveying the medium. The measuring tube vibrates, at least at times, during operation. The internal part further includes a counteroscillator affixed to the measuring tube at its inlet end for forming a first coupling zone and affixed to the measuring tube at its outlet end for forming a second coupling zone. The internal part is oscillatably held in the transducer housing by means of at least two connecting tube pieces. The at least two connecting tube pieces, via which the measuring tube also communicates, during operation, with the pipeline, are oriented with respect to one another, as well as with respect to an imaginary longitudinal axis of the measuring transducer, such that the internal part can move in the manner of a pendulum about the longitudinal axis L during operation. Measuring tube and counteroscillator are so embodied and so oriented with respect to one another that both a center of mass of the measuring tube spaced from the imaginary longitudinal axis, as well as also a center of mass of the counteroscillator spaced from the imaginary longitudinal axis lie in a common region of the measuring transducer spanned by the imaginary longitudinal axis and the measuring tube. Additionally, measuring tube and counteroscillator are so embodied and so oriented with respect to one another that the center of mass of the measuring tube is spaced farther from the longitudinal axis than the center of mass of the counteroscillator.

In a first embodiment of the invention, it is provided that each of the aforementioned centers of mass has a separation from the imaginary longitudinal axis that is greater than 10% of the greatest separation between measuring tube and imaginary longitudinal axis.

In a second embodiment of the invention, it is provided that each of the aforementioned centers of mass has a separation from the imaginary longitudinal axis that is smaller than 90% of a greatest separation between measuring tube and imaginary longitudinal axis.

In a third embodiment of the invention, it is provided that each of the aforementioned centers of mass has a separation from the imaginary longitudinal axis that is greater than 30 mm.

In a fourth embodiment of the invention, it is provided that a ratio of the separation of each of the aforementioned centers of mass to a diameter of the measuring tube is in each case greater than one. In a further development of this embodiment of the invention, it is provided that the ratio of the separation of each of the aforementioned centers of mass to a diameter of the measuring tube is in each case greater than two and smaller than ten.

In a fifth embodiment of the invention, it is provided that a diameter of the measuring tube is greater than 1 mm and smaller than 100 mm.

In a sixth embodiment of the invention, it is provided that the longitudinal axis of the measuring tube imaginarily connects the two coupling zones together.

In a seventh embodiment of the invention, it is provided that the counteroscillator has a mass which is greater than a mass of the measuring tube. In a further development of this embodiment of the invention, it is provided that a ratio of the mass of the counteroscillator to the mass of the measuring tube is greater than two.

In an eighth embodiment of the invention, it is provided that the measuring tube is essentially provided in U or V form.

In a ninth embodiment of the invention, it is provided that the counteroscillator is formed by means of counteroscillator plates arranged laterally from the measuring tube.

In a tenth embodiment of the invention, it is provided that the counteroscillator is formed by means of counteroscillator plates arranged laterally from the measuring tube and that the counteroscillator is formed by means of at least two counteroscillator plates, of which a first counteroscillator plate is arranged to the left of the measuring tube and a second counteroscillator plate is arranged to the right of the measuring tube.

In an eleventh embodiment of the invention, it is provided that the counteroscillator is formed by means of counteroscillator plates arranged laterally from the measuring tube and that each of the at least two counteroscillator plates has a curved centroidal line imaginarily extending between a contour line distal with reference to the longitudinal axis and a contour line proximal with reference to the longitudinal axis. In a further development of this embodiment of the invention, it is provided that the counteroscillator is formed by means of counteroscillator plates arranged laterally from the measuring tube and that the centroidal line of each of the at least two counteroscillator plates has, with reference to the longitudinal axis, a concave extent, at least in the region of a middle section. In another further development of this embodiment of the invention, it is provided that the counteroscillator is formed by counteroscillator plates arranged laterally from the measuring tube and that the centroidal line of each of the at least two counteroscillator plates has, with reference to the longitudinal axis, a convex extent in the region of the coupling zones. Further, it is provided that the centroidal line of each of the at least two counteroscillator plates has an essentially U or V shape, at least in the region of a middle section of the counteroscillator and/or that the centroidal line of each of the at least two counteroscillator plates is essentially parallel to a centroidal line of the measuring tube extending imaginarily within its lumen.

In a twelfth embodiment of the invention, it is provided that the counteroscillator is formed by means of counteroscillator plates arranged laterally from the measuring tube and that each of the at least two counteroscillator plates has an outer side surface of which a first edge is formed by an edge providing a contour distal with respect to the longitudinal axis and a second edge is formed by an edge providing a contour proximal with reference to the longitudinal axis. In a further development of this embodiment of the invention, it is provided that each of the at least two counteroscillator plates is so embodied and placed in the measuring transducer that both the distal, as well as also the proximal contour-providing edges of each of the at least two counteroscillator plates have a separation from the longitudinal axis different from zero at least in the region of a middle section of the counteroscillator. In such case, each of the at least two counteroscillator plates can be so embodied that a local plate height, at least in the region of a middle section of the counteroscillator, is in each case smaller than in each case in the region of the two coupling zones, wherein the local plate height itself corresponds there to a smallest separation between the distal and the proximal contour-providing edge of each of the at least two counteroscillator plates. Further, it is provided that each of the at least two counteroscillator plates is so embodied that it has a smallest plate height in the region of the middle section of the counteroscillator and/or that the plate height of each of the at least two counteroscillator plates is in each case decreasing, especially monotonically or continuously starting from a coupling zone and moving toward the middle section of the counteroscillator.

In a thirteenth embodiment of the invention, it is provided that the counteroscillator is formed by means of counteroscillator plates arranged laterally from the measuring tube and that each of the at least two counteroscillator plates has an arc, or hanger, shaped contour.

In a fourteenth embodiment of the invention, it is provided that the counteroscillator is formed by means of counteroscillator plates arranged laterally from the measuring tube and that each of the at least two plates forming the counteroscillator is arranged essentially parallel to the measuring tube.

In a fifteenth embodiment of the invention, it is provided that measuring tube and counteroscillator are mechanically connected with one another on the inlet-side by means of at least a first coupler and on the outlet-side by means of at least a second coupler.

In a sixteenth embodiment of the invention, it is provided that the connecting tube pieces include essentially straight tube segments. In a further development of this embodiment of the invention, it is provided that the connecting tube pieces are so oriented with respect to one another that the tube segments extend essentially parallel to the imaginary longitudinal axis. In such case, the connecting tube pieces can be so directed with respect to one another that the essentially straight tube segments essentially align with one another and/or with the imaginary longitudinal axis.

In a seventeenth embodiment of the invention, it is provided that the measuring tube executes during operation, at least at times, bending oscillations relative to the counteroscillator and relative to the longitudinal axis.

In an eighteenth embodiment of the invention, it is provided that measuring tube and counteroscillator execute, during operation, at least at times, and at least in part, bending oscillations of equal frequency, about the longitudinal axis. According to a further development of this embodiment of the invention, it is additionally provided that these are such bending oscillations about the longitudinal axis which are, at least in part, out of phase with one another, especially essentially of opposite phase.

In a nineteenth embodiment of the invention, it is provided that the internal part held oscillatably in the housing of the transducer has a natural lateral oscillation mode in which it oscillates during operation in accordance with deformations of the two connecting tube pieces, at least at times, relative to the transducer housing and laterally about the longitudinal axis. In a twentieth embodiment of the invention, it is provided that the internal part held oscillatably in the transducer housing has an oscillation mode in the manner of a pendulum in which it moves during operation in accordance with deformations of the two connecting tube pieces, at least at times, about the imaginary longitudinal axis with a pendulum-like motion. According to a further development of this embodiment of the invention, it is further provided that at least one natural eigenfrequency of the pendulum-like oscillation mode is smaller than a lowest oscillation frequency with which the measuring tube instantaneously vibrates and/or that at least an instantaneous natural eigenfrequency of the oscillation mode in the manner of a pendulum is always smaller than an instantaneous lowest natural eigenfrequency of the measuring tube.

In a twenty-first embodiment of the invention, it is provided that the internal part held oscillatably in the transducer housing has both an oscillation mode in the manner of a pendulum in which it moves in a pendulum-like manner during operation in accordance with deformations of the two connecting tube pieces, at least at times, about the imaginary longitudinal axis and also a natural lateral oscillation mode in which it, during operation, oscillates in accordance with deformations of the two connecting tube pieces, at least at times, relative to the transducer housing and laterally about the longitudinal axis and that the lateral oscillation mode of the internal part has a lowest eigenfrequency which is greater than a lowest eigenfrequency of the pendulum-like oscillation mode of the internal part. In a further development of this embodiment of the invention, it is further provided that a ratio of the lowest eigenfrequency of the lateral oscillation mode of the internal part to the lowest eigenfrequency of the pendulum-like oscillatory mode of the internal part is greater than 1.2 and/or that a ratio of the lowest eigenfrequency of the lateral oscillation mode of the internal part to the lowest eigenfrequency of the pendulum-like oscillatory mode of the internal part is smaller than 10. Especially, the aforementioned ratio of the lowest eigenfrequency of the lateral oscillation mode of the internal part to the lowest eigenfrequency of the pendulum-like oscillation mode of the internal part can in such case be maintained greater than 1.5 and smaller than 5.

In a twenty-second embodiment of the invention, it is provided that the internal part held oscillatably in the transducer housing has a pendulum-like oscillation mode in which it moves in the manner of a pendulum during operation in accordance with deformations of the two connecting tube pieces, at least at times, about the imaginary longitudinal axis and that at least one natural eigenfrequency of the pendulum-like oscillation mode of the internal part is smaller than a lowest oscillation frequency with which the measuring tube instantaneously vibrates and/or that at least one instantaneous natural eigenfrequency of the pendulum-like oscillatory mode of the internal part is always smaller than an instantaneous lowest natural eigenfrequency of the measuring tube. In a further development of this embodiment of the invention, it is provided that a ratio of the lowest eigenfrequency of the measuring tube to the lowest eigenfrequency of the pendulum-like oscillatory mode of the internal part is greater than 3 and/or is smaller than 20. Especially, the ratio of the lowest eigenfrequency of the measuring tube to the lowest eigenfrequency of the pendulum-like oscillatory mode of the internal part can be in such case greater than 5 and smaller than 10.

In a twenty-third embodiment of the measuring transducer of the invention, such further includes an exciter mechanism for causing measuring tube and counteroscillator to vibrate.

In a twenty-fourth embodiment of the measuring transducer of the invention, such further includes a sensor arrangement for registering oscillations, at least of the measuring tube. In a further development of this embodiment of the invention, it is provided that the sensor arrangement for registering oscillations of the measuring tube includes at least a-first sensor arranged on the inlet side at the measuring tube, as well as a second sensor arranged on the inlet side at the measuring tube. Additionally, it can be of advantage, when the sensor arrangement for registering oscillations of the measuring tube includes, further, at least a third sensor arranged on the inlet side at the measuring tube, as well as a fourth sensor arranged on the outlet side at the measuring tube. This, especially also then, when the first sensor is arranged opposite to the third sensor at the measuring tube, and the second sensor is arranged opposite to the fourth sensor at the measuring tube.

A basic idea of the invention is, especially also in contrast to the measuring transducers disclosed in U.S. Pat. No. 6,666,098, to move the center of mass of the counteroscillator closer to the longitudinal axis in comparison to the center of mass of the measuring tube. In this way, it is achieved that the counteroscillator can, without more, be embodied essentially heavier than the measuring tube, even though, however, also the above mentioned inherent, terminal, torsional oscillators formed by means of the internal part and the connecting tube pieces can, without more, also be driven or operated with the tuning proposed in U.S. Pat. No. 6,666,098. It has additionally, in such case, been shown that it can be very important for the balancing of the measuring transducer, as also discussed in U.S. Pat. No. 6,666,098, to embody the mass distributions of measuring tube and counteroscillator and, as a result, the position of the centers of mass essentially equally. Yet even more important is that, during operation, those moments which result from the movement of the vibrating measuring tube must in each case be introduced into the terminal coupling zones as much as possible under an equal angle of attack as those moments which are produced by the also vibrating counteroscillator. This, especially also with reference to an as complete as possible transformation of possible lateral imbalances into rather uncritical, pendulum-like movements of the internal part in the manner proposed in U.S. Pat. No. 6,666,098. On the one hand, it is so also possible in this manner largely, or at least significantly more effectively, to prevent the transformation of such lateral imbalances into other more damaging oscillation forms of the internal part. By the displacement of the centers of mass in the aforementioned manner, the working range of the measuring transducer can, as a result, be clearly increased, especially also in comparison to additionally that disclosed in U.S. Pat. No. 6,666,098, such that an angular mismatch arising of necessity between the two aforementioned angles of attack as a result of fluctuating density of the medium can be both negative, as well as also positive. As a result of this, it is possible to achieve in advantageous manner that the angular mismatch in the case of equal fluctuation breadth assumes, comparatively speaking, only small absolute amounts. Consequently, an optimum tuning of the oscillation characteristics of the measuring transducer, especially of its internal part, can be done for the medium to be measured during operation, especially with respect to the fluctuations to be expected for its density, and, as a result, a considerable improvement of the density-dependent zero point influenceability can be achieved.

Equally, the principle of compensation proposed in U.S. Pat. No. 6,666,098 can not only be further put into practice, but also further improved, in the respect that the counteroscillator can be embodied not only somewhat heavier but also especially somewhat more bending, and twisting, stiffer. Further, it was possible already at a comparatively small increase in mass in the order of magnitude of about ten percent to achieve an improvement of the sensitivity of more than fifty percent in comparison with the above mentioned measuring transducer of type "PROMASS H" and, as a result, also a corresponding improvement of the measurement accuracy. Especially, it was possible, besides the improvement of the density-dependent, zero point influenceability, even in the case of large deviation from the calibrated reference density of the measuring transducer, also to detect a considerable improvement of the accuracy of measurement of the inline measuring device in the case of small flow rates.

The measuring transducer of the invention distinguishes itself furthermore by the fact that, in the use of a counteroscillator of the aforedescribed kind with correspondingly higher mass, the two connecting tube pieces can, without more, be kept correspondingly short, and, consequently, also an installed total length of the measuring transducer can be significantly decreased, while maintaining an essentially constant, high quality of the dynamic oscillation decoupling. Moreover, the measuring transducer can be embodied, despite its short installed length, after as before, relatively lightly.

In the following, the invention and further advantages will be explained on the basis of an example of an embodiment presented in the figures of the drawing. Equal parts are provided in the figures with equal reference characters. In case conducive to overviewability, already mentioned reference characters are omitted in subsequent figures. The figures of the drawing show as follows:

DETAILED DESCRIPTION OF EXEMPLARY EMBODIMENTS

While the invention is susceptible to various modifications and alternative forms, exemplary embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the intended claims.

Figure 1A:
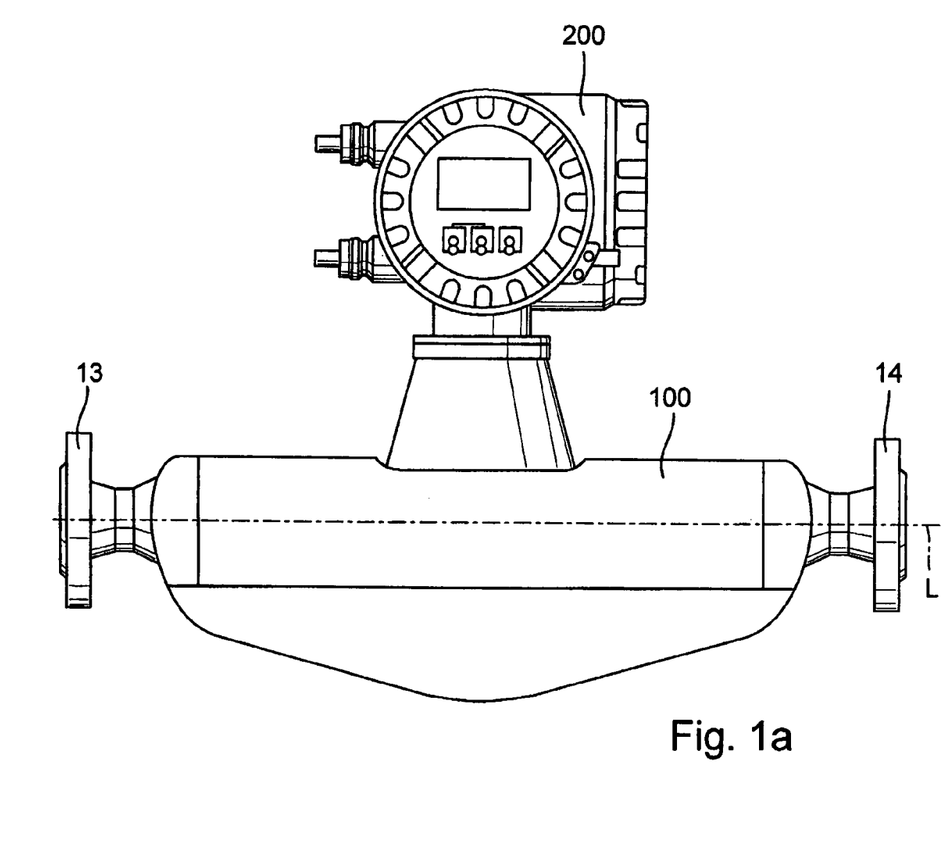
FIG. 1*a* is a side view, of an inline measuring device for media flowing in pipelines.
Figure 1B:
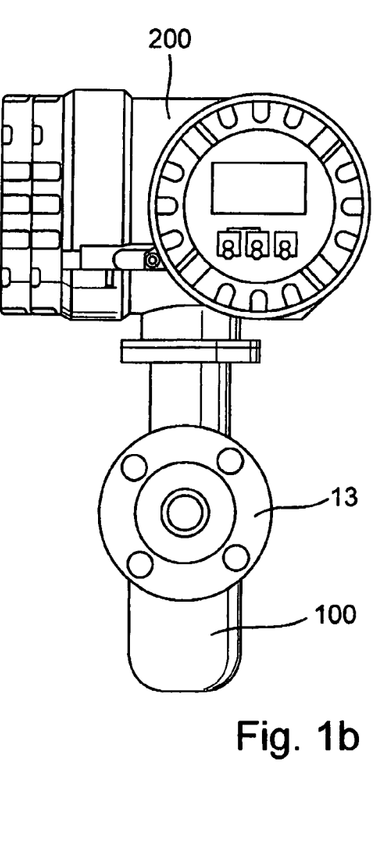
FIG. 1*b* is a front view of, an inline measuring device for media flowing in pipeline.
Figure 2:
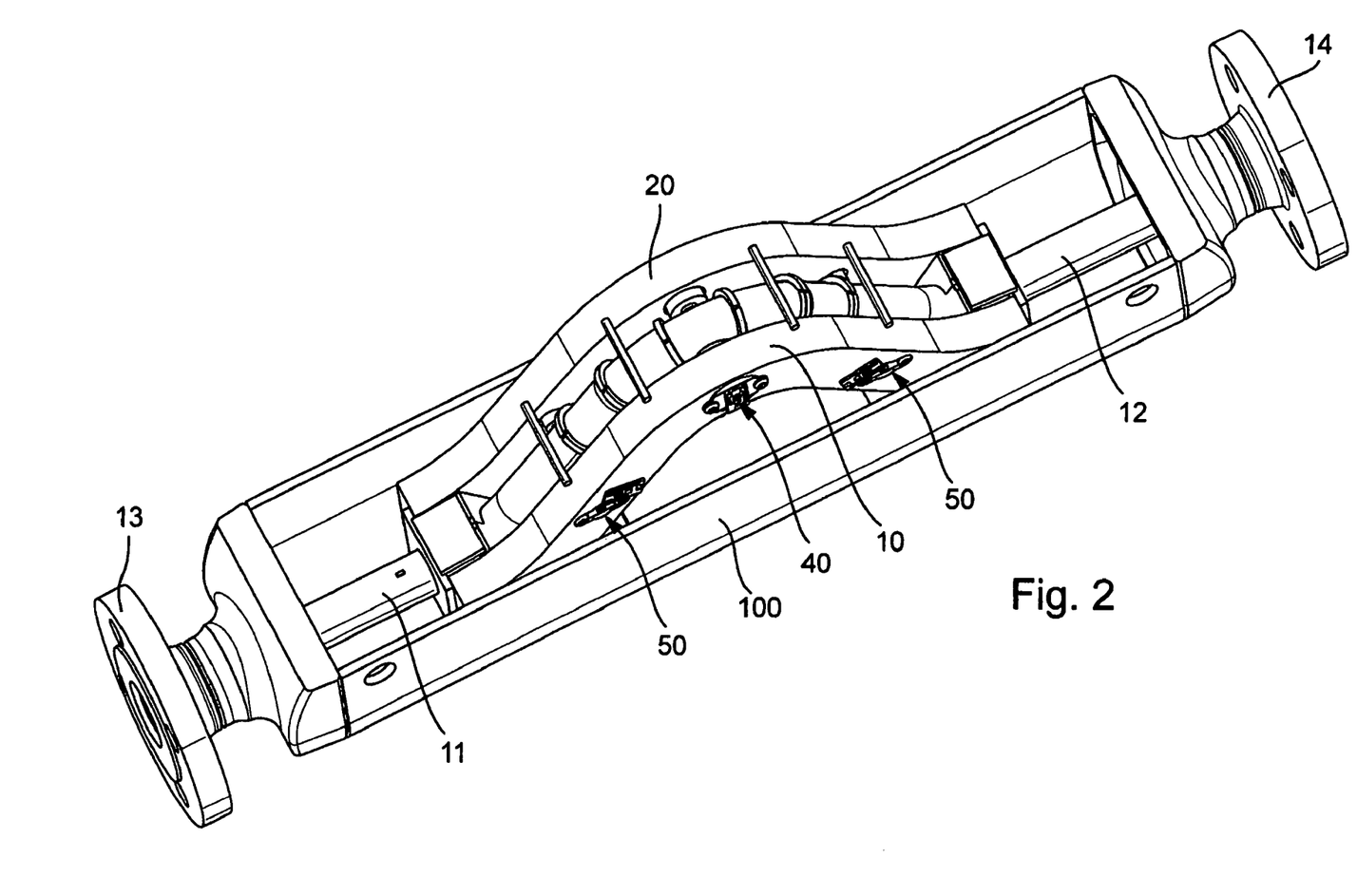
FIG. 2 is a partially sectioned, perspective view, of a measuring transducer of vibration-type suitable for an inline measuring device according to FIGS. 1*a*, 1*b*.
Figure 3:
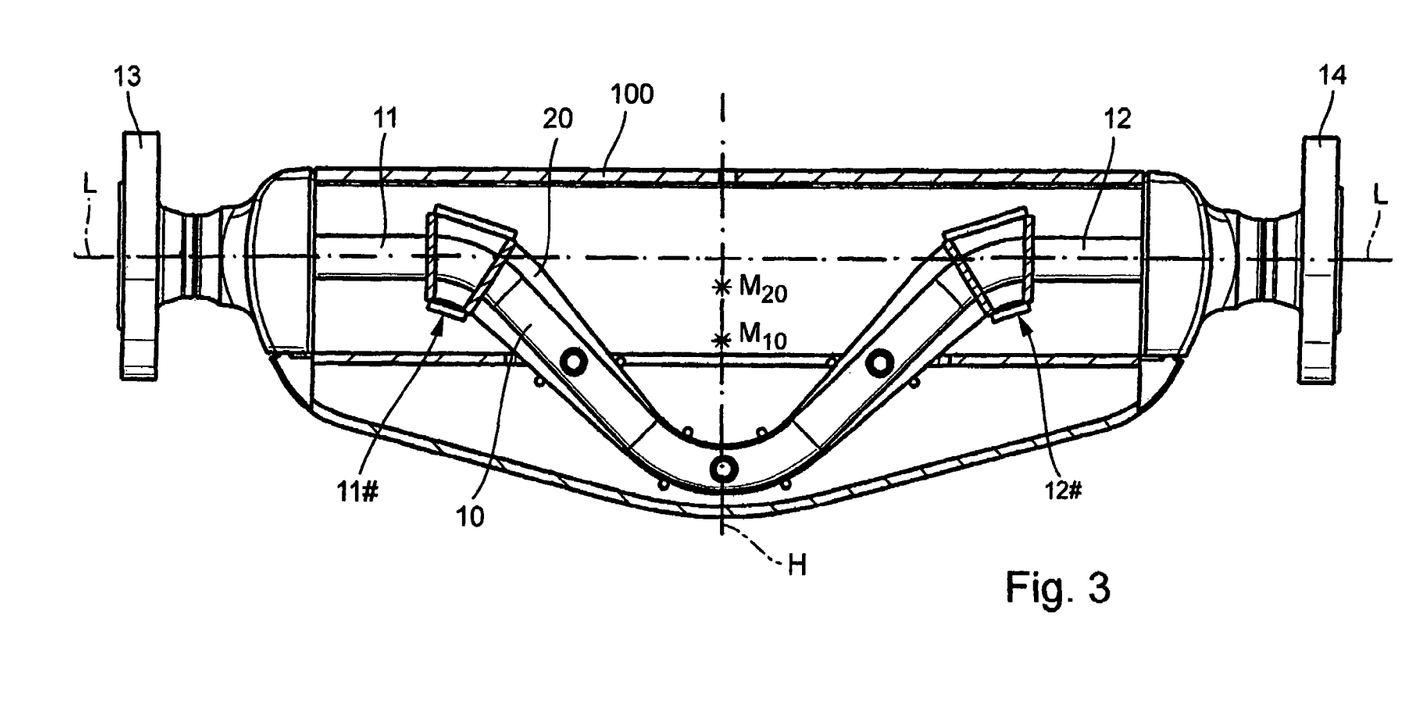
FIG. 3 is a partially sectioned, side view, of the measuring transducer of FIG. 2.

Shown in FIGS. 1*a, b* is an inline measuring device, for example, one embodied as a Coriolis mass flow measuring device, density measuring device, viscosity measuring device, or the like, installable into a pipeline, for example, a process line of an industrial plant. The inline measuring device serves for measuring and/or monitoring at least one parameter, for example, a mass flow, a density, viscosity, etc., of a medium flowing in a pipeline. The inline measuring device includes, for such purpose, a measuring transducer of vibration-type, through which, during operation, a medium to be measured flows. FIGS. 2 and 3 show, schematically, a corresponding example of an embodiment for such a measuring transducer of vibration-type. The principle mechanical construction, and the manner in which such operates, is, for the most part, quite comparable with that of the measuring transducer disclosed in U.S. Pat. No. 6,666,098. The measuring transducer serves for producing in a medium flowing therethrough mechanical reaction forces, e.g. mass flow dependent, Coriolis forces, density dependent, inertial forces and/or viscosity dependent, frictional forces, which react measurably, especially sensorially registerably, on the measuring transducer. Derived from these reaction forces, it is possible, in the manner known to those skilled in the art, to measure e.g. a mass flow m, a density ρ and/or a viscosity η of the medium. The measuring transducer includes for such purpose a transducer housing 100, as well as an internal part arranged in the transducer housing 100 for actually effecting the physical-to-electrical converting of the at least one parameter to be measured.

For conveying the medium, the internal part includes a measuring tube 10, here a single, curved measuring tube 10, which is caused to vibrate during operation and, as a result, is repeatedly elastically deformed. to execute oscillations about a static rest position. The measuring tube 10, and, as a result, also the centroidal line of the measuring tube 10, which connects the centres of mass (centroids) of the cross-sectional areas of measuring tube, extending imaginarily within the lumen, can for, example, be embodied essentially in Ω or U shape, or, as shown in FIG. 2, essentially with a V shape. Since the measuring transducer should be usable for a multiplicity of different applications, especially in the field of industrial measurements and automation technology, it is further provided that the measuring tube, depending on the application of the measuring transducer, has a diameter lying in the range between about 1 mm and about 100 mm.

For minimizing disturbing influences acting on the measuring tube 10, as well as also for reducing oscillatory energy transferred from the measuring transducer to the connected pipeline, a counteroscillator 20 is additionally provided in the measuring transducer. This is, as also shown in FIG. 2, arranged separated laterally from the measuring tube 10 in the measuring transducer and affixed to the measuring tube 10 in each case with the forming of an inlet-side first coupling zone 11#, basically defining an inlet end of the measuring tube 10, and with the formation of a second coupling zone 12# on the outlet-side, essentially defining an outlet end of the measuring tube 10. The counteroscillator 20, which in the illustrated example of an embodiment is arranged extending essentially parallel to the measuring tube 10, especially also coaxially thereto, can also be embodied, for example, tubularly or also essentially with box shape. For the latter case, the counteroscillator 20 can be formed, as also illustrated in FIG. 2, for example, by means of plates arranged on the left and right sides of the measuring tube 10.

As can be seen from a comparison of FIGS. 2 and 3, the counteroscillator 20 is mounted by means of at least one inlet-side, first coupler 31 at the inlet end 11# of the measuring tube 10 and by means of an outlet-side, second coupler 32, especially a coupler 32 essentially identical to the coupler 31, at the outlet end 12# of the measuring tube 10. Serving as couplers 31, 32 can, in such case, be e.g. simple node plates, which are secured in corresponding manner on the inlet-side and outlet-side, in each case, to the measuring tube 10 and to the counteroscillator 20. Additionally, it is possible, as in the case of the example of an embodiment shown here, to have completely closed boxes formed in each case on the inlet-side and outlet-side by means of node plates mutually separated from one another in the direction of the longitudinal axis together with protruding ends of the counteroscillator 20, or, as required, to have also partially open frames, serve as coupler 31, respectively coupler 32.

For allowing the medium to be measured to flow through, the measuring tube 10 is additionally connected to the pipeline (not shown) supplying the medium, and, then, conveying it away, via a first connecting tube piece 11 opening on the inlet-side in the region of the first coupling zone 11# and via a second connecting tube piece 12, especially one essentially identical to the first connecting tube piece 11, opening on the outlet-side in the region of the second coupling zone 12#, with each of the two connecting tube pieces 11, 12 having tube segments which are essentially straight. Advantageously, the measuring tube 10 and the two connecting tube pieces 11, 12 can be embodied as one piece, so that, for their manufacture, e.g. a single tubular stock can be used. Instead of measuring tube 10, inlet tube piece 11, and outlet tube piece 12, being formed by segments of a single, one-piece tube, these can, in case required, however, also be manufactured by means of separate, subsequently joined, e.g. welded together, stock, or pieces of stock. For manufacturing the measuring tube 10, it is furthermore appropriate to use practically any of the materials usual for such measuring transducers, e.g. steel, Hastelloy, titanium, zirconium, tantalum, etc.

As additionally shown in FIGS. 2 and 3, the transducer housing 100, especially one which is bending- and torsion-stiff in comparison to measuring tube 10, is affixed, especially rigidly, to an inlet end of the inlet-side, connecting tube piece 11 distal with reference to the first coupling zone #11, as well as to an outlet end of the outlet-side, connecting tube piece 12 distal with reference to the first coupling zone #11. Thus, as a result, the entire internal part is not only completely encased by the transducer housing 100, but, as a result of its own mass and the resilience of both connecting tube pieces 11, 12, also held oscillatably in the transducer housing 100. Additionally to accommodating the internal part, the transducer housing 100 can also serve for holding an electronics housing 200 of the inline measuring device with measuring device electronics accommodated therein. For the case in which the measuring transducer is to be mounted releasably with the pipeline, additionally, a first flange 13 is formed on the inlet-side, connecting tube piece 11 at an inlet end and a second flange 14 on the outlet-side, connecting piece 12 at an outlet end. The flanges 13, 14 can, in such case, as is quite usual for measuring transducers of. the described kind, also be integrated into the transducer housing 100, at least partially, on the ends thereof. In case required, the connecting tube pieces 11, 12 can also, however, be connected directly with the pipeline, e.g. by means of welding or brazing.

During operation of the measuring transducer, the measuring tube 10, as usual in the case of such measuring transducers of vibration type, is so excited to cantilever, or wagging, oscillations at an exciter frequency $f_{exc}$ that it deflects in essentially a natural, first eigenoscillation form in the so-called wanted mode, oscillating about the longitudinal axis L of the measuring transducer. As a result of this, thus, the measuring tube 10 executes during operation, at least at times, bending oscillations relative to counteroscillator 20 and longitudinal axis L. At the same time, also the counteroscillator 20 is excited to cantilever oscillations and indeed so such that it, at least in part, oscillates out of phase with, especially essentially with opposite phase to, the measuring tube 10 oscillating in the wanted mode. Especially, measuring tube 10 and counteroscillator 20 are, in such case, so excited that they execute during operation, at least at times and at least in part, bending oscillations of equal frequency but essentially opposite phase about the longitudinal axis L. The bending oscillations can, in such case, be so developed that they are of equal modal order and consequently, at least in the case of resting fluid, essentially of equal form. In other words, measuring tube 10 and counteroscillator 20 move then in the manner of tuning fork tines oscillating oppositely to one another. In a further embodiment of the invention, the exciter, or also wanted mode, frequency $f_{exc}$ is, in such case, so tuned that it corresponds, as much as possible, exactly to a natural eigenfrequency of the measuring tube 10, especially a lowest natural eigenfrequency of the measuring tube 10. In the case of an application of a measuring tube manufactured from stainless steel with a nominal diameter of 29 mm, a wall thickness of about 1.5 mm, a stretched length of about 420 mm, and a bridge length of about 305 mm measured from inlet end #11 to outlet end 12#, the lowest resonance frequency of the same would amount, for example, at a density of practically zero, e.g. in the case of a measuring tube filled completely with air, to about 490 Hz. Advantageously, it is further provided that also a lowest natural eigenfrequency $f_{20}$ of the counteroscillator 20 is about equal to the lowest natural eigenfrequency $f_{10}$ of the measuring tube and as a result also about equal to the exciter frequency $f_{exc}$.

For producing mechanical oscillations of the measuring tube 10 and the counteroscillator 20, the measuring tube further includes an exciter mechanism 40, especially an electrodynamic exciter mechanism. This serves for converting an electric exciter energy $E_{exc}$, e.g. one having a controlled current and/or a controlled voltage, fed, for example, by a control electronics (not shown) of the above mentioned Coriolis mass flow meter and accommodated in electronics housing 200, into an exciter force $f_{exc}$ acting, e.g. in pulse or harmonic form, on the measuring tube 10 and deflecting this in the aforementioned manner. Controls suitable for the adjusting of the exciter energy $E_{exc}$ include the control electronics shown e.g. in U.S. Pat. Nos. 4,777,833, 4,801,897, 4,879,911 or 5,009,109. The exciter force $f_{exc}$ can, as usual for measuring transducers of such type, be developed bidirectionally or unidirectionally and, in the manner known to those skilled in the art, be tuned e.g. by means of a current and/or voltage control circuit with respect to its amplitude and e.g. by means of a phase locked loop with respect to its frequency. The exciter mechanism 40 can be e.g. a simple solenoid arrangement having a cylindrical exciter coil connected to the counteroscillator 20 and flowed-through during operation by a corresponding exciter current and including a permanently magnetic armature plunging, at least at times, into the exciter coil and affixed externally, especially at the halfway point on the measuring tube 10. Additionally, e.g. also an electromagnet can serve as the exciter mechanism 40.

For detecting oscillations of the measuring tube 10, the measuring transducer additionally includes a sensor arrangement 50. Sensor arrangement 50 can be practically any sensor arrangement usual for such measuring transducers for registering the movements of the measuring tube 10, especially movements on the inlet-side and on the outlet-side and converting such into corresponding sensor signals. Thus, the sensor arrangement 50 can, e.g. in manner known to those skilled in the art, be formed by means of a first sensor 51 arranged on the measuring tube 10 on the inlet-side and a second sensor 52 arranged on the measuring tube 10 at the outlet-side. The sensors can be e.g. electrodynamic velocity sensors relatively measuring the oscillations or, however, also electrodynamic path sensors or acceleration sensors. Alternatively to or in supplementation of the electrodynamic sensor arrangements, it is also possible to use, for detecting oscillations of the measuring tube 10, resistive or piezoelectric strain gauges or opto-electronic sensor arrangements. In case required, additionally, in manner known to those skilled in the art, other sensors required for the measuring and/or operation of the measuring transducer, such as, e.g. additional oscillation sensors arranged on the counteroscillator 20 and/or on the transducer housing 100 can be provided (compare in this regard also U.S. Pat. No. 5,736,653) or, e.g. temperature sensors can be arranged on the measuring tube 10, on the counteroscillator 20 and/or on the transducer housing 100; compare in this connection also U.S. Pat. No. 4,768,384 or WO-A 00/102816.

Figure 4:
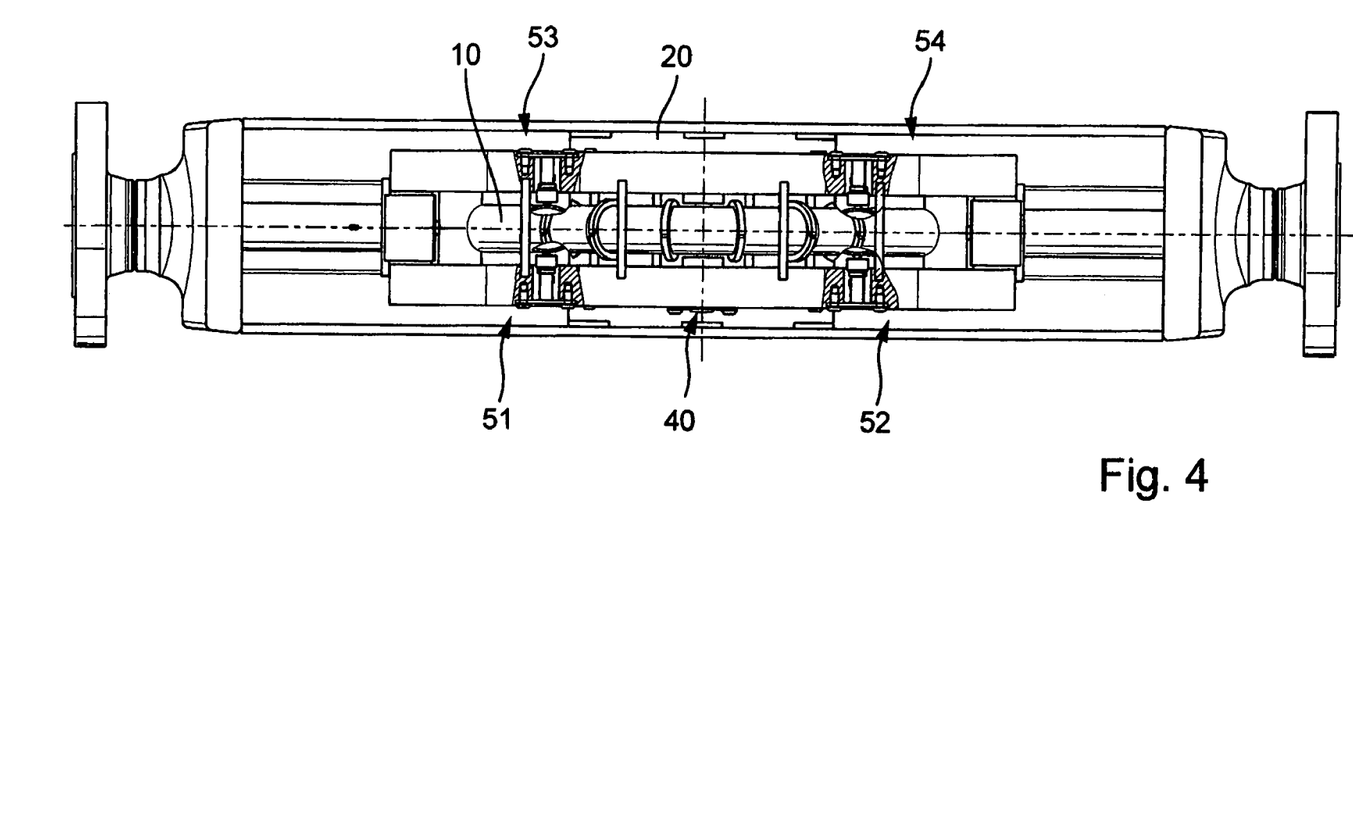
FIG. 4 is a partially sectional, bottom view, of the measuring transducer of FIG. 2.

For further improving signal quality of the sensor signals delivered by the sensor arrangement and/or for obtaining additional oscillatory information, a further development of the invention provides arranged at the measuring tube 10, in addition to the two motion, or oscillation, sensors 51, 52, two additional oscillation sensors 53, 54 reacting to movements of the measuring tube, so that, thus, the sensor arrangement 50, as also shown schematically in FIG. 4, is composed of at least four such sensors. In such case, a third sensor 53 is placed likewise on the inlet-side on the measuring tube 10 and a fourth sensor 54 is placed likewise on the outlet-side on the measuring tube 10. According to an embodiment of this further development of the invention, it is further provided that the third sensor 53 is arranged in the region of the first sensor 51, especially on the oppositely lying side of the measuring tube 10, and the fourth sensor 54 is arranged in the region of the second sensor 52, especially on the oppositely lying side of the measuring tube 10. For the case illustrated in FIG. 4, wherein, in each case, the two inlet-side sensors 51, 53 and the two outlet-side sensors 52, 54 are arranged vis-a-vis, thus lying directly opposite one another and, as seen in the oscillation direction, aligned with one another, it is possible, in this way, especially in the case of serial connecting of the two, in each case, oppositely lying sensors 51, 53, respectively 52, 54, to achieve, through a comparatively small extra effort in the implementing of the sensor arrangement 50, among other things, a significant, advantageous improvement in the signal-to-noise ratio for oscillation measurement signals delivered thereby. For simplifying both the construction of the sensor arrangement 50 and also the evaluation of the oscillation measurement signals delivered thereby, according to a further embodiment, it is additionally provided that the oscillation sensors forming the sensor arrangement 50 are essentially equal in structure.

For the case provided for operation, wherein the medium is flowing in the pipeline and, consequently, the mass flow m is different from zero, the measuring tube 10 vibrating in the above described manner induces in the through-flowing medium also Coriolis forces. These in turn act on the measuring tube 10 and, so, effect an additional, sensorially registerable deformation of the same essentially according to a natural, second eigenoscillation form. An instantaneous feature of this so-called Coriolis mode superimposed with equal frequency on the excited, wanted mode is, in such case, especially with respect to their amplitudes, also dependent on the instantaneous mass flow m. A second eigenoscillation form can be, as usual in the case of measuring transducers with curved measuring tube, e.g. the eigenoscillation form of the antisymmetric, twist mode, thus that in which the measuring tube 10 executes, as already mentioned, also rotational oscillations about an imaginary vertical axis H directed perpendicular to the longitudinal axis L and lying in a single plane of symmetry of the illustrated measuring transducer.

For the quite usual and, as a result, to be expected case, that, during operation, the density of the medium flowing in the measuring tube, and, consequently accompanying therewith, also the mass distribution in the internal part, changes considerably, the force equilibrium between the vibrating measuring tube 10 and the counteroscillator 20, likewise vibrating in the above described manner, is disturbed. When the transverse forces resulting therefrom, acting in the internal part at equal frequency with the oscillations of the measuring tube 10 cannot be compensated, the internal part suspended on the two connecting tube pieces 11, 12 is deflected laterally from an assigned, static, installed position. In this way, transverse forces can, at least in part, also act on the connected pipeline via connecting tube pieces 11, 12, by way of which the measuring tube 10 communicates, as already mentioned, during operation with the pipeline and cause this, as well as also the inline measuring device as such, to consequently vibrate as such in undesired manner. Furthermore, such transverse forces can also lead to the fact that the measuring tube 10 is, due to a, from oscillatory details point-of-view, non-uniform suspending of the internal part, or also of the entire measuring transducer, caused e.g. by practically unavoidable manufacturing tolerances, excited additionally to disturbance oscillations of equal frequency, for example, additional cantilever oscillations according to the second eigenoscillation form, which then, especially due to the fact of the equal oscillation frequency, are no longer distinguishable practically sensorially from the actual Coriolis mode.

Besides the lateral disturbance oscillations, the internal part suspended in the transducer housing can additionally also execute pendulum-like oscillations about the longitudinal axis L, wherein the coupling zones are rotated about the longitudinal axis and the connecting tube pieces 11, 12 are twisted. In corresponding manner, also the two coupling zones and, consequently, also the two couplers 31, 32 experience a corresponding torsional rotation about the longitudinal axis L, i.e. also they oscillate and indeed, with respect to one another, in essentially opposite phase. In other words, the internal part oscillatably held in the transducer housing has a pendulum-like, oscillatory mode, in which it moves as a pendulum during operation, accompanied by deformations of the two connecting tube pieces, at least at times, about the imaginary longitudinal axis L. In such case, the vibrating measuring tube 10 and the counteroscillator 20 additionally execute common pendulum-like movements about the longitudinal axis L which are essentially of equal phase, at least at resting medium, to one another and to the cantilever oscillations of the counteroscillator 20, provided that a mass $m_{20}$ of the counteroscillator 20 is smaller than an instantaneous total mass of the measuring tube 10 conveying the medium. For the opposite case, that the total mass of the measuring tube 10 conveying the medium is smaller than the mass of the counteroscillator 20, these pendulum-like motions of the internal part can be embodied with equal phase to the cantilever oscillations of the measuring tube 10.

On the other hand, however, the internal part suspended oscillatably in the transducer housing 100 has itself at least one lateral oscillation mode determined predominantly by the bending spring stiffness of the connecting tube pieces 11, 12, as well as its instantaneous total mass. In this lateral oscillation mode, the internal part would, accompanied by corresponding bending deformations of the two connecting tube pieces 11, 12, oscillate in resonance, during operation, relative to the transducer housing 100 and laterally about the longitudinal axis L, to the extent that it is correspondingly pushed against, to so excite it. Equally, the internal part also has at least one natural, pendulum-like, oscillatory mode, determined primarily by the torsional spring stiffness of the connecting tube pieces 11, 12, as well as an instantaneous total moment of inertia about the longitudinal axis L, in which it moves, to the extent that it is correspondingly excited, in resonance as a pendulum during operation, accompanied by corresponding deformations in the form of twisting of the two connecting tube pieces about the imaginary longitudinal axis L.

Luckily, it is possible, as already discussed in U.S. Pat. No. 6,666,098, to transform also the residual transverse forces affecting the lateral oscillation mode of the internal part by suitable tuning or matching of the connecting tube pieces 11, 12 and the internal part largely into much less critical pendulum-like oscillations of the entire internal part about the longitudinal axis L and as a result to largely prevent the otherwise damaging lateral oscillations of the internal part. For such purpose, it is necessary to adjust (by appropriate dimensioning of the two connecting tube pieces 11, 12, as well as the two couplers 31, 32) only one natural eigenfrequency, $f_1$, of the first torsional oscillator formed on the inlet-side by means of the connecting tube piece 11 and the coupler 31, defining essentially the inlet-side coupling zone 11#, and one natural eigenfrequency, $f_2$, of the second torsional oscillator formed equally by means of the connecting tube piece 12 and the coupler 32, defining essentially the outlet-side coupling zone 11#, in such a manner that the two eigenfrequencies, $f_1$, $f_2$, are about equal to the exciter frequency, $f_{exc}$, at which the measuring tube 10, at least predominantly, oscillates; compare in this connection also U.S. Pat. No. 6,666,098. As a result of possible pendulum-like oscillations of the internal part at the wanted frequency, $f_{exc}$, the two aforementioned torsional oscillators are then caused to oscillate torsionally about the longitudinal axis L. For adjusting the eigenfrequencies, $f_1$, $f_2$, an inlet-side mass moment of inertia (here essentially provided by means of the inlet-side coupler 31 and a torsional stiffness of the associated connecting tube piece 11) about the longitudinal axis L, as well as an outlet-side mass moment of inertia (here provided essentially by means of the coupler 32 and a torsional stiffness of the outlet-side connecting tube piece 12) about the longitudinal axis L are to be correspondingly tuned to one another. In the case of the measuring transducer illustrated here, besides the node plates and the, in each case, terminally protruding, plate ends, also those tube segments extending between the two respective node plates of the couplers 31, 32 are to be appropriately taken into consideration in the sizing of the mass moment of inertia for the tuning of the inlet-side torsional eigenmode.

On the basis of a tuning of wanted mode and torsional eigenmode in the described manner, it is achieved that the internal part which moves during operation in the manner of a pendulum with equal frequency with the measuring tube 10 oscillating at the exciter frequency $f_{exc}$, practically exactly drives the inlet-side and outlet-side torsional oscillators in an intrinsic eigenmode. For this case, the two torsional oscillators, oscillating at their respective eigenfrequencies, $f_1$, $f_2$, and also compelled to have equal phase with the internal part, oppose its torsional oscillations with practically no, or only very small, counter moments. Consequently, the internal part is so rotationally softly journaled during operation that it can be considered as being practically completely decoupled as to oscillations from the two connecting tube pieces 11, 12. On the basis of the fact that the internal part, despite a practically complete decoupling, moves as a pendulum during operation about the longitudinal axis L and does not rotate, then also no total rotational impulse of the internal part can exist. Consequently, however, also a lateral total impulse, almost directly dependent on the total rotary impulse, especially in the case of similar mass distributions in the measuring tube 10 and the counteroscillator 20, and, consequently, also dependent therefrom, lateral impulses, which can be transmitted from the internal part to the outside, are likewise both practically equal to zero. For the desired case, thus that the pendulum movement of the internal part occurs during operation in the range of the respective instantaneous eigenfrequencies of the two torsional oscillators, the measuring tube can execute a pendulum-like motion, together with the counteroscillator, practically free of transverse forces and torsional moments about the longitudinal axis L. As a result, in the case of this balance, or also decoupling, mechanism, density dependent imbalances lead primarily to changes of oscillation amplitudes solely of the pendulum-like oscillations of the internal part, however, in any case to negligibly small lateral displacements of the same out of the installed static position assigned to it. As a result of this, the measuring transducer can be dynamically balanced within a comparatively broad working range, largely independently of the density role of the fluid and, so, its sensitivity to internally produced transverse forces can be significantly decreased.

It has now been found that, in the case of measuring transducers of the described kind, especially also in the case of the implementing of the aforedescribed decoupling mechanism, not only the rotationally soft mechanical coupling of the internal part to the transducer housing and to the connected pipeline is of importance. In surprising manner, especially important also is that, during operation, those moments which result from the movement of the vibrating measuring tube are in each case introduced, as much as possible, into the terminal coupling zones at a same angle of attack as those moments which are produced by the likewise vibrating counteroscillator. However, it has also been shown further that, due to fluctuating density of the medium, a considerable angular mismatch can arise between the angles of attack.

In order to hold this practically unavoidably fluctuating, angular mismatch as much as possible within boundaries which can be handled for the desired working range, measuring tube 10 and counteroscillator 20 are, in the case of the measuring transducer of the invention, so embodied and so oriented with respect to one another that both a center of mass, $M_{10}$, of the measuring tube 10 spaced from the imaginary longitudinal axis L, as well as also a center of mass, $M_{20}$, of the counteroscillator 20 spaced from the imaginary longitudinal axis L, lie, as shown schematically in FIG. 3, in a region of the measuring transducer spanned in common by the imaginary longitudinal axis L and the measuring tube 10. Moreover, measuring tube 10 and counteroscillator 20 are furthermore so embodied and so oriented with respect to one another that, at least in the rest position, the center of mass, $M_{10}$, of the measuring tube 10 is farther from the longitudinal axis L than the center of mass, $M_{20}$, of the counteroscillator. According to a further embodiment of the invention, it is additionally provided that each of the two aforementioned centers of mass, $M_{10}$, $M_{20}$, has a separation from the imaginary longitudinal axis which is greater than 10% of a greatest separation measurable between measuring tube 10 and the imaginary longitudinal axis L. For an implementing of the measuring transducer with usual installation measures, this would mean, practically, that each of the centers of mass, $M_{10}$, $M_{20}$, has a distance from the imaginary longitudinal axis L greater than 30 mm. Additionally, it has been found that a ratio of the separation of each of the centers of mass, $M_{10}$, $M_{20}$, to the diameter of the measuring tube 10 should be, in each case, greater than one, especially at least two. Additionally, it was possible to discover that it can be of advantage, when each of the centers of mass, $M_{10}$, $M_{20}$, has a separation from the imaginary longitudinal axis L which is smaller than 90% of the greatest separation between measuring tube 10 and imaginary longitudinal axis L. According to a further embodiment of the invention, it is, therefore, additionally provided, that the ratio of the separation of each of the centers of mass, $M_{10}$, $M_{20}$, to the diameter of the measuring tube 10 is in each case greater than 2 and smaller than 10.

By the displacement of the centers of mass in the aforementioned manner, the working range of the measuring transducer can be markedly increased, especially also in comparison to the disclosure of U.S. Pat. No. 6,666,098, such that an angular mismatch between the two aforementioned angles of attack as a result of fluctuating medium density can be both negative as well as also positive, and consequently assumes absolute magnitudes only about half as large and, as a result, is comparatively small. Consequently, also the density-dependent zero-point influenceability of the measuring transducer can also be significantly decreased.

In, order beyond this, to implement an as robust as possible decoupling of the internal part of the measuring transducer also from disturbing in-couplings on the part of the measuring tube 10, especially also to assure that the internal part itself begins to oscillate in the manner of a pendulum as much as possible exclusively due to the acting decoupling mechanism and as much as possible not due to the excitings of other eigenresonances, a further embodiment of the invention provides that at least one natural eigenfrequency of its pendulum-like oscillation mode is smaller than a lowest oscillation frequency with which the measuring tube 10 is caused to vibrate instantaneously, for example, thus, the wanted frequency $f_{exc}$. For this, the internal part is additionally so embodied that at least a lowest instantaneous natural eigenfrequency of the pendulum-like oscillatory mode of the internal part is always smaller than the instantaneously lowest natural eigenfrequency of the measuring tube 10.

As a result of the fact that the decoupling mechanism implemented in the proposed manner rests essentially on a more structural tuning of the aforementioned torsional oscillators and the internal part, a tuning which during operation can practically not be changed from the exterior, naturally quite a very small detuning is to be expected on the basis of changing characteristics of the medium as compared to conventional measuring transducers without the above described decoupling mechanism. These parameters relevant for the tuning can be, besides the density, for example, the viscosity of the medium and/or its temperature and, in accompaniment therewith, the temperature of the internal part itself. In order also, for such cases, to be able to provide a measuring transducer as well balanced as possible, a further embodiment of the invention provides that the internal part is so sized that a natural eigenfrequency of its pendulum-like oscillatory mode is smaller than a lowest oscillation frequency with which the measuring tube 10 vibrates instantaneously or that at least an instantaneous natural eigenfrequency of the pendulum-like oscillatory mode of the internal part is always smaller than an instantaneously lowest natural eigenfrequency of the measuring tube 10. It has been found in this case that a ratio of the lowest eigenfrequency of the measuring tube 10 to the lowest eigenfrequency of the pendulum-like oscillatory mode of the internal part should be greater than 3 and, conversely, does not need to be greater than 20. It has, in this case, additionally been found that for most cases of application it can be sufficient that this ratio of the lowest eigenfrequency of the measuring tube 10 to the lowest eigenfrequency of the pendulum-like oscillatory mode of the internal part is kept in a comparatively narrow working range about between 5 and 10.

According to a further embodiment of the invention, the internal part and the two connecting tube pieces 11, 12 are so tuned to one another that the lateral oscillatory mode of the internal part exhibits a lowest eigenfrequency which is greater than a lowest eigenfrequency of the pendulum-like oscillatory mode of the internal part. Especially it is provided in such case, that the internal part and the two connecting tube pieces 11, 12 are so matched to one another that a ratio of the lowest eigenfrequency of the lateral oscillatory mode of the internal part to the lowest eigenfrequency of the pendulum-like oscillatory mode of the internal part is greater than 1.2. Additionally, it is provided that this ratio of the lowest eigenfrequency of the lateral oscillatory mode of the internal part to the lowest eigenfrequency of the pendulum-like oscillatory mode of the internal part is so tuned that it is smaller than 10. It has additionally been found in such case that, for most cases of application, it can be sufficient to keep this ratio of the lowest eigenfrequency, $f_L$, of the lateral oscillatory mode of the internal part to the lowest eigenfrequency, $f_P$, of the pendulum-like oscillatory mode of the internal part in a relatively narrow working range between about 1.5 and 5.

According to a further embodiment of the invention, it is additionally provided that the two connecting tube pieces 11, 12 are so oriented with respect to one another as well as with respect to a longitudinal axis imaginarily connecting the two coupling zones 11#, 12# that the internal part, accompanied by twistings of the two connecting tube pieces 11, 12, can move in the manner of a pendulum about the longitudinal axis L. For this purpose, the two connecting tube pieces 11, 12 are to be so directed with respect to one another that the essentially straight tube segments extend essentially parallel to the imaginary longitudinal axis L, as well as being essentially aligned to this and to one another. Since the two connecting tube pieces 11, 12 in the example of an embodiment illustrated here, are embodied essentially straight over their entire length throughout, they are, accordingly, directed essentially aligned entirely with one another, as well as with the imaginary longitudinal axis L.

According to an embodiment of the invention, it is furthermore provided that, as a compromise between optimum spring action and acceptable installed size of the measuring transducer, on the one hand, a length of each of the connecting tube pieces 11, 12 corresponds in each case at most to 0.5 times a shortest separation between the two coupling zones 11#, 12#. In order to be able to provide as compact a measuring transducer as possible, each of the two connecting tube pieces 11, 12 has especially a length, which is, in each case, smaller than 0.4 times the shortest separation between the two coupling zones.

For improving the above-described decoupling mechanism, the counteroscillator 20, in a further embodiment of the invention, is essentially made heavier than the measuring tube 10. In a further development of this embodiment of the invention, in such case, a ratio of the mass, $M_{20}$, of the counteroscillator 20 to a mass, $M_{10}$, of the measuring tube 10 is made greater than two. Especially, measuring tube 10 and counteroscillator 20 are additionally so embodied that the latter has a mass, $M_{20}$, which is also greater than a mass of the measuring tube 10 filled with the medium to be measured. In order that the counteroscillator 20, in spite of its comparatively high mass, $M_{20}$, has an eigenfrequency which lies about at the eigenfrequency of the measuring tube excited in the wanted mode, or at least in its range, the counteroscillator 20 is additionally so embodied, at least in the case of this embodiment of the invention, that it is, in corresponding manner, as well, bending-stiffer than the measuring tube 10.

For implementing the counteroscillator 20, especially one which is also more heavily, equally, however, also more bending-stiffly embodied, and for simplified tuning of the same to the measuring tube 10 and/or the terminal torsional oscillators in the described manner, in a further embodiment of the invention, it is additionally provided that it is at least partially formed by means of plates 21, 22 arranged laterally to the measuring tube 10. In the case of the example of an embodiment shown here, the counteroscillator is formed by means of at least two curved counteroscillator plates 21, 22, of which a first counteroscillator plate 21 is located to the left of measuring tube 10 and a second counteroscillator plate 22 is arranged to the right of the measuring tube 10. Each of the at least two, here, essentially formed arcuately or hanger-like, counteroscillator plates 21, 22 has an outer lateral surface, of which a first edge is formed by an edge providing a contour distal with reference to the longitudinal axis and a second edge is formed by an edge providing a contour proximal with reference to the longitudinal axis. In the example of an embodiment illustrated here, additionally, each of the at least two counteroscillator plates 21, 22 forming the counteroscillator 20 is arranged essentially parallel to the measuring tube 10. In a further embodiment of the invention, each of the at least two counteroscillator plates 21, 22 is furthermore so embodied and so placed in the measuring transducer relative to the measuring tube 10 that both the distal, as well as also the proximal contour providing edge of each of the at least two counteroscillator plates 21, 22, at least in the region of a central section of the counteroscillator 20 has a separation from the longitudinal axis L different from zero.

As also illustrated in FIGS. 2 and 3, furthermore, each of the at least two counteroscillator plates 21, 22 is so embodied that, at least in the region of a central section of the counteroscillator 20, a local plate height is in each case smaller than, in each case, in the region of the two coupling zones. The local plate height corresponds in such case, in each case, to a smallest separation which on a selected location of the corresponding counteroscillator plates is measured between the distal and the proximal contour-providing edge of each of the at least two counteroscillator plates 21, 22. According to a further development of the invention, each of the at least two counteroscillator plates 21, 22 has additionally, in the region of the central section of the counteroscillator 20, a smallest plate height. Further, it is provided that the plate height of each of the at least two counteroscillator plates 21, 22, in each case, decreases starting from a coupling zone and moving toward the central section of the counteroscillator 20.

In a further embodiment of the invention, each of the at least two plates 21, 22 forming the counteroscillator 20 has an essentially hanger-shaped contour or silhouette. In corresponding manner, a centroidal line of each of the at least two counteroscillator plates 21, 22 imaginarily extending between a contour line distal with reference to the longitudinal axis L and a contour line proximal with reference to the longitudinal axis is likewise so-curved. As explained with respect to the measuring tube, the imaginary centroidal line of each of said plates connects centroids of its respective cross-sectional areas. On the basis of the hanger-shaped form of the counteroscillator 20, the centroidal line of each of the at least two counteroscillator plates 21, 22 has a concave curvature at least in the range of a central section with reference to the longitudinal axis and a curvature convex with reference to the longitudinal axis at least in the region of the coupling zones.

Measuring tube 10 and counteroscillator 20 are, as already mentioned, as required, to be so embodied that they, in the case of an external spatial form as similar as possible, also have equal, or at least mutually similar, mass distributions. In a further embodiment of the invention, it is, therefore, provided that the plates 21, 22 forming the counteroscillator 20 and, as a result, also the counteroscillator 20 itself, have a curvature essentially comparable with, or at least similar to, that of the curved measuring tube. Equally, also the centroidal line of each of the at least two counteroscillator plates 21, 22 is essentially equally as curved, at least in the region of a middle section of the counteroscillator, as is the measuring tube 10. Accordingly, the counteroscillator plates 21, 22 forming the counteroscillator 20 and consequently both the counteroscillator 20 as well as also the entire internal part, have, in the example of an embodiment shown here, essentially a U-shaped or V-shaped, curved silhouette. Equally, in this example of an embodiment, also the centroidal line of each of the at least two counteroscillator plates 21, 22 is formed essentially U or V-shaped, at least in the region of a middle section of the counteroscillator 20 situated between the two coupling zones. In a further embodiment, the counteroscillator plates 21, 22 are additionally so formed and so arranged with reference to the measuring tube 10 that the centroidal line of each of the at least two counteroscillator plates 21, 22 extends essentially parallel to the centroidal line of the measuring tube 10 extending imaginarily inside of its lumen.

By a combination of hanger-shaped contour of the counteroscillator 20, on the one hand, and the plate height tapering toward the center, on the one hand, the counteroscillator 20, and, as a result, also the internal part, can be adjusted very simply both with respect to the mass distributions, especially the relative positions of the centers of mass, $M_{10}$, $M_{20}$, as well as also largely independently thereof, with respect to the above stated eigenfrequencies $f_{20}$, $f_L$, $f_P$. Beyond this, also the-decoupling mechanism implemented by means of the terminal torsional oscillators can in this. way be tuned largely independently of the aforementioned criteria, since, on the one hand, indeed, the protruding ends of the counteroscillator plates together with the utilized node plates provide the predominant contribution to the required mass moment of inertia, and, on the other hand, however, their height can, in each case, be suitably selected within wide limits, essentially without influencing the above mentioned other oscillatory characteristics of the counteroscillator 20.

In order to enable an as simple as possible matching of the counteroscillator 20 to a mass or a mass distribution effective in the case of the actual measuring tube 10, it is also possible to attach, especially releasably, to the counteroscillator 20 additionally mass balancing elements 21 serving as discrete, added masses. Alternatively or in supplementation, a corresponding mass distribution can be realized over the counteroscillator 20 also by the forming of longitudinal or annular grooves. A mass and/or mass distribution of the counteroscillator 20, respectively the internal part, ultimately suited for the particular application can, without more, be initially determined e.g. by means of finite element calculations and/or by means of corresponding calibration measurements. The parameters then to be selected in the case of a concrete measuring transducer for optimum tuning of the inlet-side and outlet-side angles of attack, thus corresponding masses, mass distributions, and/or mass moments of inertia of measuring tube 10 and counteroscillator 20 and geometric dimensions derived therefrom can be determined, e.g. in the manner known per se to those skilled in the art, by means of finite element or other computer based, simulation calculations coupled with corresponding calibration measurements.

The measuring transducer of the invention is, due to its good dynamic balancing, especially suited for application in a Coriolis mass flow meter, a Coriolis mass flow/density meter, or in a Coriolis mass flow/density/viscosity meter, as provided for media with densities fluctuating significantly during operation.

While the invention has been illustrated and described in detail in the drawings and forgoing description, such illustration and description is to be considered as exemplary not restrictive in character, it being understood that only exemplary embodiments have been shown and described and that all changes and modifications that come within the spirit and scope of the invention as described herein are desired to protected.

What is claimed is:

1. A measuring transducer of vibration type for a medium flowing in a pipeline, comprising:
    a transducer housing; and
    an internal part arranged in said transducer housing, said internal part including at least a curved measuring tube serving for the conveying of the medium and vibrating, at least at times, during operation, and a counteroscillator affixed externally to said measuring tube forming a first coupling zone on an inlet-side of said measuring tube and a second coupling zone on an outlet-side of said measuring tube, wherein:
    said internal part is mounted oscillatably in said transducer housing, at least by means of two connecting tube pieces via which said measuring tube communicates during operation with the pipeline, and which are so oriented with respect to one another, as well as with respect to an imaginary longitudinal axis of the measuring transducer, that said internal part can move, during operation, with pendulum-like motion about said longitudinal axis; and
    said measuring tube and said counteroscillator are so embodied and so directed with respect to one another that both a center of mass of said measuring tube spaced from the imaginary longitudinal axis, as well as also a center of mass of said counteroscillator spaced from the imaginary longitudinal axis, lie in a common region of the measuring transducer spanned by the imaginary longitudinal axis and said measuring tube, and the center of mass of said measuring tube additionally is spaced farther from the longitudinal axis than the center of mass of said counteroscillator.

2. The measuring transducer as claimed in claim 1, wherein:
    each of the centers of mass has a separation from the imaginary longitudinal axis which is greater than 10% of the greatest separation between said measuring tube and the imaginary longitudinal axis; and/or each of the centers of mass has a separation from the imaginary longitudinal axis which is smaller than 90% of the greatest separation between said measuring tube and the imaginary longitudinal axis; and/or each of the centers of mass has a separation from the imaginary longitudinal axis which is greater than 30 mm; and/or a diameter of said measuring tube is greater than 1 mm and smaller than 100 mm; and/or the longitudinal axis of the measuring transducer imaginarily connects the two coupling zones together; and/or said measuring tube is embodied essentially in a U-shape or in a V-shape; and/or said measuring tube and said counteroscillator are mechanically connected together on the inlet-side by means of at least a first coupler and on the outlet-side by means of at least a second coupler; and/or said measuring tube executes, during operation, at least at times, bending oscillations relative to said counteroscillator and the longitudinal axis.

3. The measuring transducer as claimed in claim 1, wherein:

a ratio of the separation of each of the centers of mass to a diameter of said measuring tube is, in each case, greater than 1.

4. The measuring transducer as claimed in claim 3, wherein:

the ratio of the separation of each of the centers of mass to a diameter of said measuring tube is, in each case, greater than 2 and smaller than 10.

5. The measuring transducer as claimed in claim 1, wherein:

said counteroscillator has a mass which is greater than the mass of said measuring tube.

6. The measuring transducer as claimed in claim 5, wherein:

a ratio of the mass of said counteroscillator to the mass of said measuring tube is greater than 2.

7. The measuring transducer as claimed in claim 2, wherein:

said counteroscillator is formed by means of counteroscillator plates arranged laterally to said measuring tube.

8. The measuring transducer as claimed in claim 7, wherein:

said counteroscillator is formed by means of at least two counteroscillator plates of which a first counteroscillator plate is arranged to the left of said measuring tube and a second counteroscillator plate is arranged to the right of said measuring tube; and/or each of said at least two counteroscillator plates includes an outer, lateral surface, of which a first edge is formed by a contour-providing edge distal with respect to the longitudinal axis, and,a second edge formed by a contour-providing edge proximal with respect to the longitudinal axis; and/or each of said at least two counteroscillator plates is so embodied and so placed in the measuring transducer that both the distal, as well as also the proximal, contour-providing edge of each of said at least two counteroscillator plates show, at least in a middle-section region of said counteroscillator, a separation from the longitudinal axis different from zero; and/or each of said at least two counteroscillator plates is so embodied that, at least in the region of a middle section of said counteroscillator, a local plate height is, in each case, smaller than, in each case, in the region of the two coupling zones, wherein the local plate height thereat, in each case, corresponds to the smallest separation between the distal and proximal contour-providing edges of each of said at least two counteroscillator plates; and/or p1 each of said at least two counteroscillator plates is so embodied that it has in the middle-section region of said counteroscillator the smallest plate height; and/or each of said at least two counteroscillator plates is so embodied that the plate height of each of said at least two counteroscillator plates, in each case, decreases, especially monotonically or continuously, starting from a coupling zone toward the middle section of said counteroscillator; and/or each of said at least two counteroscillator plates has an arc, or hanger, shaped contour; and/or each of said at least two plates forming said counteroscillator is arranged essentially parallel to said measuring tube.

9. The measuring transducer as claimed in claim 7, wherein:

each of said at least two counteroscillator plates shows a curved imaginary centroidal line connecting centroids of cross-sectional areas of the respective counteroscillator plate.

10. The measuring transducer as claimed in claim 9, wherein:

the centroidal line of each of said at least two counteroscillator plates extends between a contour line of the perspective counteroscillator plate distal with respect to the longitudinal axis and a contour line of the perspective counteroscillator plate proximal with respect to the longitudinal axis of the measuring transducer; and/or the centroidal line of each of said at least two counteroscillator plates includes, with reference to the longitudinal axis of the measuring transducer, a concave curvature, at least in a middle-section region; and/or the centroidal line of each of said at least two counteroscillator plates includes, with reference to the longitudinal axis of the measuring transducer, in each case, a convex curvature, at least in a coupling zones region; and/or the centroidal line of each of said at least two counteroscillator plates has an essentially U-shape or V-shape, at least a middle-section region of said counteroscillator; and/or the centroidal line of each of said at least two counteroscillator plates extends essentially parallel to a centroidal line of said measuring tube extending imaginarily within its lumen.

11. The measuring transducer as claimed in claim 1, wherein:

said connecting tube pieces have essentially straight tube segments.

12. The measuring transducer as claimed in claim 10, wherein:

said connecting tube pieces are so oriented with respect to one another that the tube segments extend essentially parallel to the imaginary longitudinal axis; and/or the connecting tube pieces are so oriented with respect to one another that the essentially straight tube segments align essentially with one another; and/or wherein the connecting tube pieces are so oriented with respect to one another that the essentially straight tube segments align essentially with the imaginary longitudinal axis.

13. The measuring transducer as claimed in claim 1, wherein:

said measuring tube and said counteroscillator execute, at least at times and at least in part, bending oscillations of equal frequency about the longitudinal axis.

14. The measuring transducer as claimed in claim 13, wherein:
said measuring tube and said counteroscillator execute during operation, at least at times, bending oscillations about the longitudinal axis which are, at least in part, out of phase with one another, especially essentially of opposite phase.

15. The measuring transducer as claimed in claim 1, wherein:
said internal part held oscillatably in said transducer housing has a natural lateral oscillation mode in which it oscillates during operation, accompanied by deformations of said two connecting tube pieces, at least at times, relative to said transducer housing and laterally about the longitudinal axis.

16. The measuring transducer as claimed in claim 1, wherein:
said internal part held oscillatably in said transducer housing has a pendulum-like, oscillatory mode, in which it moves during operation in the manner of a pendulum, accompanied by deformations of said two connecting tube pieces, at least at times, about the imaginary longitudinal axis.

17. The measuring transducer as claimed in claim 15, wherein:
at least a natural eigenfrequency of the pendulum-like, oscillatory mode is smaller than the lowest oscillation frequency with which said measuring tube instantaneously vibrates; and/or
at least one instantaneous natural eigenfrequency of the pendulum-like oscillatory mode is always smaller than an instantaneous lowest natural eigenfrequency of said measuring tube.

18. The measuring transducer as claimed in claim 1, wherein:
said internal part held oscillatably in said transducer housing shows a natural lateral oscillation mode in which it oscillates during operation, accompanied by deformations of said two connecting tube pieces, at least at times, relative to said transducer housing and laterally about the longitudinal axis; and
said internal part held oscillatably in said transducer housing has a pendulum-like oscillatory mode in which it moves in the manner of a pendulum, at least at times, about the imaginary longitudinal axis, during operation, accompanied by deformations of said two connecting tube pieces, and
the lateral oscillatory mode of said internal part has a lowest eigenfrequency which is greater than the lowest eigenfrequency of the pendulum-like oscillatory mode of said internal part.

19. The measuring transducer as claimed in claim 18, wherein:
a ratio of the lowest eigenfrequency of the lateral oscillatory mode of said internal part to the lowest eigenfrequency of the pendulum-like oscillatory mode of said internal part is greater than 1.2; and/or
a ratio of the lowest eigenfrequency of the lateral oscillatory mode of said internal part to the lowest eigenfrequency of the pendulum-like oscillatory mode of said internal part is smaller than 10; and/or
a ratio of the lowest eigenfrequency of the lateral oscillatory mode of said internal part to the lowest eigenfrequency of the pendulum-like oscillatory mode of said internal part is greater than 1.5 and smaller than 5; and/or
at least one natural eigenfrequency of the pendulum-like oscillatory mode of said internal part is smaller than the lowest oscillation frequency with which said measuring tube instantaneously vibrates, and/or
at least an instantaneous natural eigenfrequency of the pendulum-like oscillatory mode of said internal part is always smaller than the instantaneously lowest natural eigenfrequency of said measuring tube; and/or
a ratio of the lowest eigenfrequency of said measuring tube to the lowest eigenfrequency of the pendulum-like oscillatory mode of said internal part is greater than 3; and/or
a ratio of the lowest eigenfrequency of said measuring tube to the lowest eigenfrequency of the pendulum-like oscillatory mode of said internal part is smaller than 20; and/or
a ratio of the lowest eigenfrequency of said measuring tube to the lowest eigenfrequency of the pendulum-like oscillatory mode of said internal part is greater than 5 and smaller than 10.

20. The measuring transducer as claimed in claim 1, further comprising:
an exciter mechanism for causing said measuring tube and said counteroscillator to vibrate.

21. The measuring transducer as claimed in claim 1, further comprising:
a sensor arrangement for registering oscillations, at least of said measuring tube.

22. The measuring transducer as claimed in claim 21, wherein:
said sensor arrangement for registering oscillations of said measuring tube includes at least a first sensor arranged on the inlet-side at said measuring tube and a second sensor arranged on the outlet-side at said measuring tube; and/or
said sensor arrangement for registering oscillations of said measuring tube further includes at least a third sensor arranged on the inlet-side at said measuring tube and a fourth sensor arranged on the outlet-side at said measuring tube; and/or
said first sensor lies opposite to said third sensor and said second sensor lies opposite to said fourth sensor.

23. The use of a measuring transducer as claimed in claim 1, in an inline measuring device, especially a Coriolis mass-flow measuring device, density measuring device, and/or viscosity measuring device, which serves for measuring a medium flowing in a pipeline.

* * * * *